US008706202B2

(12) United States Patent
O'Brien et al.

(10) Patent No.: US 8,706,202 B2
(45) Date of Patent: Apr. 22, 2014

(54) IMPLANTABLE MEDICAL DEVICE WITH ADAPTIVE SIGNAL PROCESSING AND ARTIFACT CANCELLATION

(75) Inventors: Richard J. O'Brien, Hugo, MN (US); D. Curtis Deno, Andover, MN (US); David A. Anderson, Stanchfield, MN (US); David R. Bloem, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 699 days.

(21) Appl. No.: 12/687,946

(22) Filed: Jan. 15, 2010

(65) Prior Publication Data

US 2010/0179444 A1 Jul. 15, 2010

Related U.S. Application Data

(60) Provisional application No. 61/144,943, filed on Jan. 15, 2009.

(51) Int. Cl.
*A61B 5/04* (2006.01)

(52) U.S. Cl.
USPC .......................................................... 600/509

(58) Field of Classification Search
USPC ................................ 607/4–28; 600/508–528
See application file for complete search history.

(56) References Cited

U.S. PATENT DOCUMENTS

| 5,423,869 | A | 6/1995 | Poore et al. |
| 5,634,469 | A * | 6/1997 | Bruder et al. ................. 600/512 |
| 6,115,628 | A | 9/2000 | Stadler et al. |
| 6,198,952 | B1 | 3/2001 | Miesel |
| 6,408,198 | B1 | 6/2002 | Hanna et al. |
| 6,497,655 | B1 | 12/2002 | Linberg et al. |
| 2003/0065269 | A1 | 4/2003 | Vetter et al. |
| 2004/0230105 | A1 | 11/2004 | Geva et al. |
| 2004/0230128 | A1 * | 11/2004 | Brockway et al. ............ 600/510 |

(Continued)

FOREIGN PATENT DOCUMENTS

| WO | 2004091719 | 10/2004 |
| WO | 2008064682 | 6/2008 |

OTHER PUBLICATIONS (PCT/US2010/021126) PCT Notification of Transmittal of the International Search Report and the Written Opinion of the International Search Authority, Mailed Mar. 29, 2010, 10 pages.

(Continued)

*Primary Examiner* — Christopher D Koharski
*Assistant Examiner* — Nadia Ahmad
(74) *Attorney, Agent, or Firm* — Evans M. Mburu; Stephen W. Bauer

(57) ABSTRACT

A medical device having a sensor sensing an n-dimensional signal during a first known variable condition and during a second known variable condition different from the first known variable condition, a processor performing principal component analysis (PCA) on the sensed n-dimensional signal to generate a first template corresponding to a principal component of variation associated with the first known variable condition and a second template corresponding to a principal component of variation associated with the second known variable condition, a storage device storing the first template and the second template, and a controller detecting a patient condition in response to the stored templates.

24 Claims, 10 Drawing Sheets

(56) References Cited

U.S. PATENT DOCUMENTS

| | | |
|---|---|---|
| 2005/0049492 A1 | 3/2005 | Sweeney et al. |
| 2005/0197586 A1 | 9/2005 | Pearlman |
| 2006/0064136 A1 | 3/2006 | Wang |
| 2006/0116593 A1 | 6/2006 | Zhang et al. |
| 2006/0211949 A1 | 9/2006 | Sweeney et al. |
| 2007/0208265 A1 | 9/2007 | Coudere et al. |
| 2008/0051670 A1 | 2/2008 | Banet et al. |
| 2008/0132799 A1 | 6/2008 | Xue |
| 2008/0221401 A1 | 9/2008 | Derchak et al. |

OTHER PUBLICATIONS (PCT/US2010/021124) PCT Notification of Transmittal of the International Search Report and the Written Opinion of the International Search Authority, Mailed Mar. 29, 2010, 10 pages.

Manly, Bryan F.J., Multivariate Statistical Methods: A Primer 3rd Edition, Chapman & Hall, 2004, pp. 75-90.

* cited by examiner

IMPLANTABLE MEDICAL DEVICE WITH ADAPTIVE SIGNAL PROCESSING AND ARTIFACT CANCELLATION

REFERENCE TO RELATED APPLICATIONS

The present non-provisional U.S. patent application claims the benefit of U.S. Patent Application 61/144,943, filed provisionally on Jan. 15, 2009, and entitled "IMPLANTABLE MEDICAL DEVICE WITH ADAPTIVE SIGNAL PROCESSING AND ARTIFACT CANCELLATION", incorporated herein by reference in it's entirety.

TECHNICAL FIELD

The disclosure relates generally to medical devices and, in particular, to a medical device and associated method for processing sensor signals.

BACKGROUND

Implantable medical devices (IMDs) used to monitor physiological conditions or to deliver therapy typically include one or more physiological sensors. Examples of IMDs include hemodynamic monitors, pacemakers, implantable cardioverter defibrillators (ICDs), myostimulators, neurological stimulators, drug delivery devices, insulin pumps, glucose monitors, etc. The physiological sensors used in conjunction with IMDs supply time-varying signals that are related to a physiological condition from which a patient's state or a need for therapy can be assessed.

Chronically implanted sensors function in an environment with changing artifact and signal characteristics, as well as serious power constraints. In order to provide the best therapy or diagnosis, it is important to identify, from the physiological signals produced by sensors, which signal or signals contains desired information regarding the physiological condition being monitored. It is also important to cancel or reduce the effects of artifacts within the sensor signals. This can be challenging in the use of chronically implanted physiological sensors, which can produce multiple sensor signals having differing signal responses under differing patient conditions.

DETAILED DESCRIPTION

Figure 1:
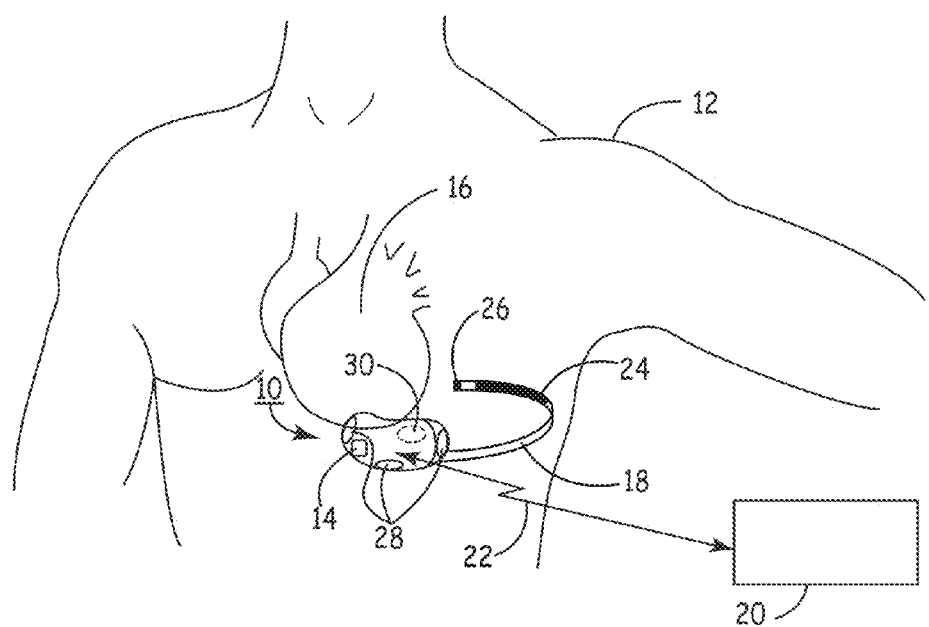
FIG. 1 is an illustration of one embodiment of an IMD in which signal processing methods described herein may be implemented.

In the following description, references are made to illustrative embodiments. It is understood that other embodiments may be utilized without departing from the scope of the invention. For purposes of clarity, the same reference numbers may in some instances be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

As used herein, a "multi-dimensional signal" is any signal comprising multiple signal components or "dimensions" which may be separated, for example, in time, frequency, space or by sensor type. Sensor types may include, but are not limited to, electrical sensors (e.g. electrodes), mechanical sensors (e.g., pressure transducers, motion transducers, etc.), acoustical sensors, optical sensors, and chemical sensors (e.g., pH sensors, glucose sensors, etc.). In one example, a multi-dimensional signal, also referred to herein as an "n-dimensional signal," includes n different signal frequencies, such as a multi-wavelength optical signal or a multi-wavelength acoustical signal. In another example, an n-dimensional signal may be an ECG signal including n different sensing electrode vectors used to acquire the ECG signal. A posture sensor, such as a three-dimensional accelerometer, may produce a three dimensional signal corresponding to patient posture or movement in x-, y-, and z-directions. A motion sensor detecting heart wall motion may detect heart motion in x-, y- and z-directions. In still other embodiments, an n-dimensional signal may include multiple signals acquired from different sensor types.

Each dimension of a multi-dimensional signal can be used to define an axis in an n-dimensional coordinate system such that a digitized, time-varying, multi-dimensional signal can be plotted in the coordinate system, allowing observation of the signal variation in each dimension. A multi-dimensional signal may be a signal acquired from a single sensor but separable into multiple dimensions. Examples of a single sensor producing a signal separable into multiple dimensions include an optical sensor detecting multiple light wavelengths or an acoustical sensor detecting multiple sound frequencies. Alternatively, a multi-dimensional signal may be multiple signals acquired from more than one sensor with each sensor signal defining a dimension in a coordinate system in which the n-dimensional signal can be plotted. For example, an EGM/ECG signal, a blood pressure signal and an oxygen saturation signal may be plotted in 3-dimensional space by plotting each signal along the x-, y-, or z-axis of the 3D space.

As used herein, the term "variable" is used to refer to any physiological or non-physiological phenomenon that influences the multi-dimensional signal by causing a response or change in the signal as the variable changes over time. A variable that influences the multi-dimensional signal and is of interest for detecting a patient condition is referred to herein as a "variable of interest". Other variables that influence the multi-dimensional signal but are not of direct interest for detecting the patient condition are referred to herein as "artifacts".

FIG. 1 is an illustration of one embodiment of an IMD in which signal processing methods described herein may be implemented. IMD 10 is shown embodied as a subcutaneous ICD used to monitor the heart 16 of patient 12 and deliver electrical stimulation therapies as needed. IMD 10 is merely one example of a medical device which may acquire a multi-dimensional signal. It is recognized the signal processing and analysis methods described herein may be implemented in any medical device, including implantable and external medical devices, which employ one or more physiological sensors that generate a physiological signal having multiple signal dimensions. As described above, different signal dimensions may relate to different signal frequencies, different sensor positions within the body, different operating frequencies of the sensor or sensors, or other signal aspects separable according to time, frequency, space or sensor type.

The term "physiological sensor" as used herein refers to any sensor, such as an electrode or transducer, that is responsive to a physiological phenomenon and generates a signal correlated to the physiological phenomenon. Such sensors may be responsive to electrical, chemical or mechanical phenomenon. Examples of physiological sensors include, but are not limited to, electrodes, optical sensors, pressure sensors, acoustic sensors, pH or other blood chemistry sensors, motion sensors such as accelerometers and MEMs-based sensors.

In the example of FIG. 1, IMD 10 includes an optical sensor 30. Optical sensor 30 is shown incorporated along the housing 14 of IMD 10. For example optical sensor components such as light emitters, light detectors and sensor electronics, may be located within housing 14 adjacent a window formed in housing 14 to allow light signals to be emitted and received by sensor 30. IMD 10 is implanted in a posterior, subcutaneous position. Sensor 30 may be positioned along housing 14 such that sensor 30 faces centrally, toward muscle tissue beneath IMD 10. Other arrangements of an optical sensor in an IMD system are possible, including arrangements in which an optical sensor is carried by a lead extending from IMD 10.

IMD 10 includes housing 14 for enclosing IMD circuitry. A connector (not explicitly shown in the view of FIG. 1) is provided along housing 14 for electrically coupling a subcutaneous sensing and cardioversion/defibrillation therapy delivery lead 18 to circuitry enclosed by housing 14.

Subcutaneous lead 18 includes a distal defibrillation coil electrode 24 and a distal sensing electrode 26 and a proximal connector pin (not shown) for connection to IMD 10 via the IMD connector. IMD 10 further includes multiple electrodes 28, incorporated along housing 14. Electrodes 28 are positioned along the periphery of the housing 14 and connected via feedthroughs to electronic circuitry within housing 14. Electrodes 28 shown in FIG. 1 may be positioned to form orthogonal signal vectors though other embodiments may include any number of subcutaneous housing-based electrodes. Any of the electrodes 28, sensing electrode 26, and coil electrode 24 may be selected in any combination for sensing subcutaneous ECG signals for use in monitoring a patient's heart rhythm and timing the delivery of anti-arrhythmia therapies.

ECG signals sensed by IMD 10 can be used for detecting cardiac arrhythmias such as ventricular tachycardia (VT) and ventricular fibrillation (VF). Optical sensor 30 generates a time-varying optical signal that varies in response to changes in the perfusion of a volume of tissue adjacent to sensor 30. The optical sensor signal may be used by IMD 10 in detecting or confirming a patient condition, such as VT or VF, which would cause a change in local tissue perfusion adjacent sensor 30.

Sensor 30 generally includes a light emitting portion and a light detecting portion. The light emitting portion emits light through a window in housing 14. The light emitting portion may include two or more light emitters, such as light emitting diodes (LEDs), emitting light at separate wavelengths. The emitted light is scattered by a tissue volume adjacent to or in contact with IMD 10 at the implant site. The light detecting portion includes an optoelectronic device such as a photodetector which generates an electrical signal in response to the scattered light incident upon the window and the detector. The detected light may be separated into the wavelengths corresponding to the separately emitted wavelengths thus producing a multi-dimensional optical signal. The sensor signal is used by IMD 10 in detecting or confirming a patient condition, e.g., a cardiac arrhythmia, which in turn may trigger the delivery of a therapy by IMD 10, such as a defibrillation shock. For a general example of an optical sensor that may be used in conjunction with an IMD, reference is made to U.S. Pat. No. 6,198,952 issued to Miesel, hereby incorporated herein by reference in its entirety.

The electrical signals generated by the photodetector may be analyzed using an amplitude approach or an integration approach. In the amplitude approach, the amplitude of the detector signal is examined directly, e.g., for the presence of an alternating signal amplitude response correlated to blood flow pulsatility. In the integration approach, an integrator is included in the sensor 30 for integrating the detector signal, for example using a capacitor. The signal may be integrated over fixed time intervals, which may be on the order of 0.10 to 100 ms for example. The magnitude of the integrated signal at the end of the fixed time interval is stored as a signal value and corresponds to scattered light received by the detector during the fixed time interval.

Alternatively, the photodetector signal may be integrated until a predetermined integrated signal magnitude is reached and the time interval required to reach the predetermined magnitude is stored as a sample data point. When the integration approach is used to obtain sensor signal values, the fixed integration time interval or the predetermined integrated signal magnitude are selected to allow the signal values to be acquired at or above a sampling frequency needed to ascertain a periodicity of the pulsatile signal that corresponds to an expected range of heart rates, or the frequency of another physiological condition of interest. For example, a maximum heart rate may be on the order 240 beats per minute. As such, a desired sampling rate may be approximately 30 to 50 Hz such that about 10 signal values points are acquired during each 250 ms cardiac cycle.

Reflectance is the inverse of a measured integrated photodetector time interval. In some uses of an optical sensor, reflectance is the measurement of primary interest. Reflectance measurements can be corrected for offset and ambient light effects in a straight forward manner using subtraction operations.

A reflectance signal measured using optical sensor 30 will be influenced by multiple variables. For example, pulsatility of blood flow through the tissue is one variable that influences each wavelength (i.e., dimension) of a multiple-wavelength signal. Each wavelength may be influenced in varying degrees by the blood flow pulsatility. A pulsatile or alternating current (AC) signal response to the pulsatility of blood flow through the tissue will be present during normal sinus heart rhythm. The optical signal response will change with changing heart rhythms. The pulsatility of blood flow through the tissue is generally referred to hereafter as the "cardiac variable" or "cardiac pulsatility variable" because this variable will cause an optical signal response to changes in heart rhythm that allows the presence of certain heart rhythms to be detected, e.g., normal sinus rhythm, tachycardia or fibrillation. However, the cardiac variable will not be the only variable influencing the multiple-wavelength signal generated by sensor 30.

In particular, a measured reflectance may also vary with respiration, patient body motion, tissue encapsulation or other changes in tissue composition in the vicinity of sensor 30 and other possible variables. Each of these variables may produce different signal responses in the multi-wavelength sensor signal. As such, each wavelength of detected light will include different information relating to a variable of interest, e.g. the cardiac variable, and all other variables influencing the signal. As indicated previously, all other variables influencing the multi-dimensional signal which are not of interest for detecting a patient state or condition can be referred to as "artifacts". For example, for the purposes of detecting a cardiac rhythm, the cardiac variable is the variable of interest while other variables can be considered to be artifact, e.g. respiration, body motion, patient posture, tissue composition changes, and so on.

In stating that artifacts are not variables of interest is not to say that these variables do not change with a particular patient state or condition being detected but merely that these variables are not the primary variable relied upon in an algorithm designed to detect a particular patient state. For example, the cardiac variable may be the variable of interest for detecting VF, yet patient position, activity, and respiration may change in the presence of VF, perhaps even in a predictable manner. These variables, however, are secondary variables which are not direct indicators of VF and can change as the result of other patient conditions not related to changes in heart rhythm.

In various embodiments, one or more variables may be variables of interest for detecting a patient state and one or more variables may be considered artifacts. As will be described herein, signal processing methods can use Principal Component Analysis (PCA) to evaluate the principal components of variation of a multi-dimensional signal in response to differing variable conditions. These signal processing methods allow the analysis of multi-dimensional signal response to the variable(s) of interest and cancellation of principal components of variation of artifacts from the variable(s) of interest.

The signal processing methods described herein may be implemented in IMD 10 for analyzing a multi-wavelength signal from optical sensor 30. In other embodiments, the signal processing methods may be performed to analyze a multi-vector ECG signal sensed by IMD 10, e.g. using two or more sensing vectors acquired by electrodes 24, 26 and 28. It is recognized that other medical devices may include other sensors, carried by a lead extending from an IMD, incorporated in or on an IMD, or as a separate sensing device. Any multi-dimensional signal acquired by a medical device may be processed and analyzed utilizing PCA methods as described below.

IMD 10 includes telemetry circuitry (not shown in FIG. 1) enabled for bi-directional communication with an external device 20 via a telemetry link 22. External device 20 may be a programmer, home monitor, or another medical monitoring or therapy delivery device. Signal processing and analysis methods may be fully implemented in IMD 10 or across multiple medical devices. In one embodiment, signal processing and analysis is fully implemented in IMD 10 and resulting data made available to a clinician by transmitting data from IMD 10 to external device 20. In alternative embodiments, n-dimensional signal data may be acquired by IMD 10 and transferred to external device 20 with portions of the signal processing and analysis methods implemented in external device 20.

Figure 2:
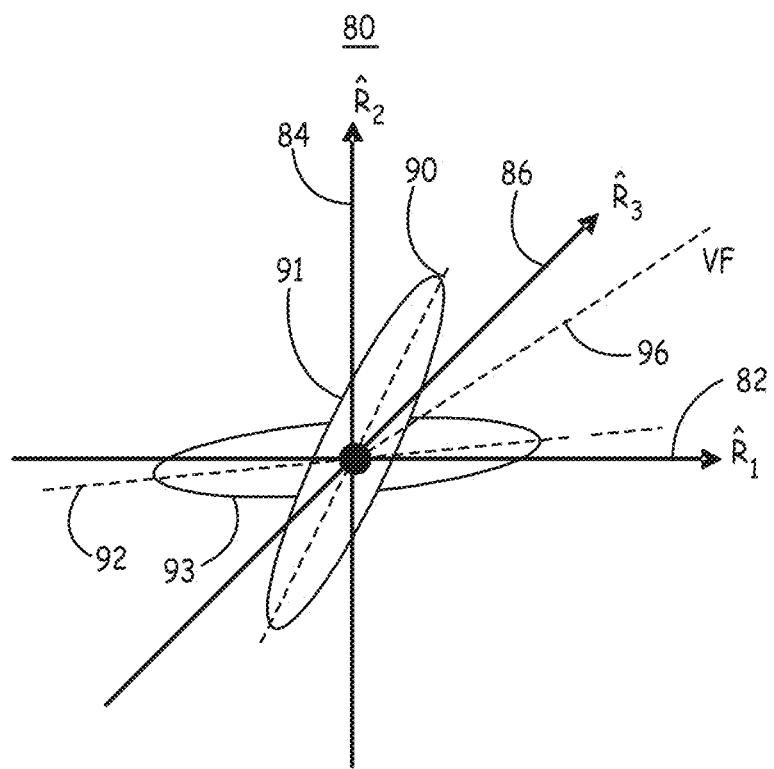
FIG. 2 is a diagram illustrating concepts of Principal Component Analysis applied to a multi-dimensional optical signal.

FIG. 2 is a diagram illustrating concepts of PCA applied to a multi-dimensional signal. PCA is a linear transformation of data to an n-dimensional coordinate system. Basic theory of PCA is described, for example, in Manly B. F. J., *Multivariate Statistical Methods: A Primer* $3^{rd}$ *Edition*. Chapman & Hall, 2004, pp 75-90, or in the web-published article "A tutorial of Principal Components Analysis" by Lindsay I. Smith, Feb. 26, 2002. In the illustrative example of FIG. 2, a three-dimensional coordinate system 80 is defined for a three-dimensional sensor signal. In this example, a three-wavelength optical sensor signal is used to illustrate the concept of an n-dimensional signal and coordinate system, however, it is recognized that any multi-dimensional signal can be processed using the methods described herein.

The three-wavelength optical signal can be plotted in the three-dimensions of system 80. Values for reflectance measurements for a first wavelength, R1, are plotted relative to the x-axis 82. Values for reflectance measurements for a second wavelength, R2, are plotted relative to the y-axis 84, and reflectance measurements for a third wavelength, R3, are plotted relative to the z-axis 86.

As will be described herein, a principal component of variation of the multi-dimensional signal under known variable conditions can be determined using PCA. In PCA, the greatest variance of the data along a projection in the n-dimensional coordinate system is defined to lie along an axis referred to as the "first principal component". The second greatest variance of the data defines a second axis, and so on. PCA can be used to efficiently model multi-dimensional data using fewer dimensions. In practice, the first principal component of the signal data is determined under known variable conditions and stored as a template to reflect the greatest variance of the multi-dimensional signal under the known variable conditions. Other principal components associated with smaller variation can be ignored.

For example, as shown in FIG. 2, during normal sinus rhythm, a known condition for a cardiac pulsatility variable, the multi-wavelength reflectance signal points fall primarily within a region 91 with the greatest variation occurring primarily along an axis 90. Axis 90 can be identified as the first principal component of the three-dimensional reflectance signal data using PCA, as will be described in detail herein. Likewise, a known condition for a body motion variable, for example walking, may produce signal data falling primarily within a region 93 characterized by a first principal component defined by axis 92. The first principal component represented by axis 92 for the known condition for the body motion variable is distinct from the cardiac variable first principal component axis 90 during normal sinus rhythm at rest. During VF, the first principal component of the three-dimensional reflectance signal may be represented by yet another unique axis 96. As such, using PCA, a primary axis representing the greatest variation of the multi-dimensional signal data can be determined for a variable of interest and for artifacts under different known variable conditions.

The second and third principal components, or component directions of the signal data may also be determined for each variable condition. These components are not drawn in FIG. 2 for the sake of clarity; however these components would be orthogonal to the first principal component axes 90 and 92. These orthogonal principal components would represent the axis along which the second greatest and the third greatest variation of the data occurs for the given variable conditions.

A monitored multi-dimensional signal can then be analyzed using one or more principal component(s) of the multi-dimensional signal determined under known variable conditions to detect the patient state based on the monitoring signal. For example, if a monitoring signal deviates from the principal component 90 for normal sinus rhythm and toward a VF principal component 96, a VF detection may be made or confirmed. Variation of the multi-dimensional signal due to artifacts may be cancelled using the principal components of the artifacts determined under known variable conditions. The use of PCA for canceling artifact in a multi-dimensional signal will be described in greater detail below. By canceling artifact, an n-dimensional signal can be reduced to fewer dimensions, e.g., a 1-dimensional signal, which retains significant variation associated with the variable of interest. The reduced-dimensional signal enables simpler detection algorithms to be performed than algorithms which evaluate all of the dimensions of the original multi-dimensional signal. Retaining the greatest variation of the original signal in the reduced-dimensional signal promotes accurate detection of a corresponding patient condition.

In the illustrative example of FIG. 2, changes in the pattern of a three-dimensional optical sensor signal due to changes in a cardiac condition and artifacts are shown. The concept of plotting a multi-dimensional signal in n-dimensional space, however, for observing patterns in the data that represent a physiological condition of the patient may be applied to any sensed physiological signals. By plotting the multi-dimensional signal in an n-dimensional space, trends of the data which represent a change in a physiological condition may be observed. The change in the physiological condition may be a non-pathological or pathological change. A distinct physiologic state, whether normal or pathological, can be plotted in n-dimensional space using a multi-dimensional signal and, in this way, be mathematically separable from other physiologic states. A clinician may be able to observe patterns in the plotted multi-dimensional signal data for patient diagnosis and prognosis. Patterns in the plotted multi-dimensional signal data may further provide useful information in overall patient management, e.g. managing pharmacological therapies, dietary recommendations, exercise or activity recommendations, and medical device-delivered therapies.

Patterns in the plotted multi-dimensional signal data may be more readily observed to be indicative of a particular physiological condition than when parallel observation or analysis of individual signals (dimensions) of a multi-dimensional signal is performed. For example, once the primary component of three-dimensional optical sensor signal data is known for different physiological conditions, such as different cardiac conditions, activity conditions, and respiration conditions, the first principal component axes representing those conditions can be plotted in an n-dimensional space. Patient data may then be plotted in the n-dimensional space as it is acquired. Patterns of the data trending toward any of the plotted first principal component axes, or variation of the data occurring primarily along a principal component axis, is evidence of the physiological condition corresponding to that axis. In the example of FIG. 2, optical sensor signal data from a patient may be acquired during unknown conditions and plotted in the three dimensional coordinate system 80 shown in FIG. 2. As variation in the plotted signal data occurs along any one of the principal component axes 90, 92 or 96, the physiological state of the patient can be determined as corresponding to the condition represented by that principal component axis.

Figure 3:
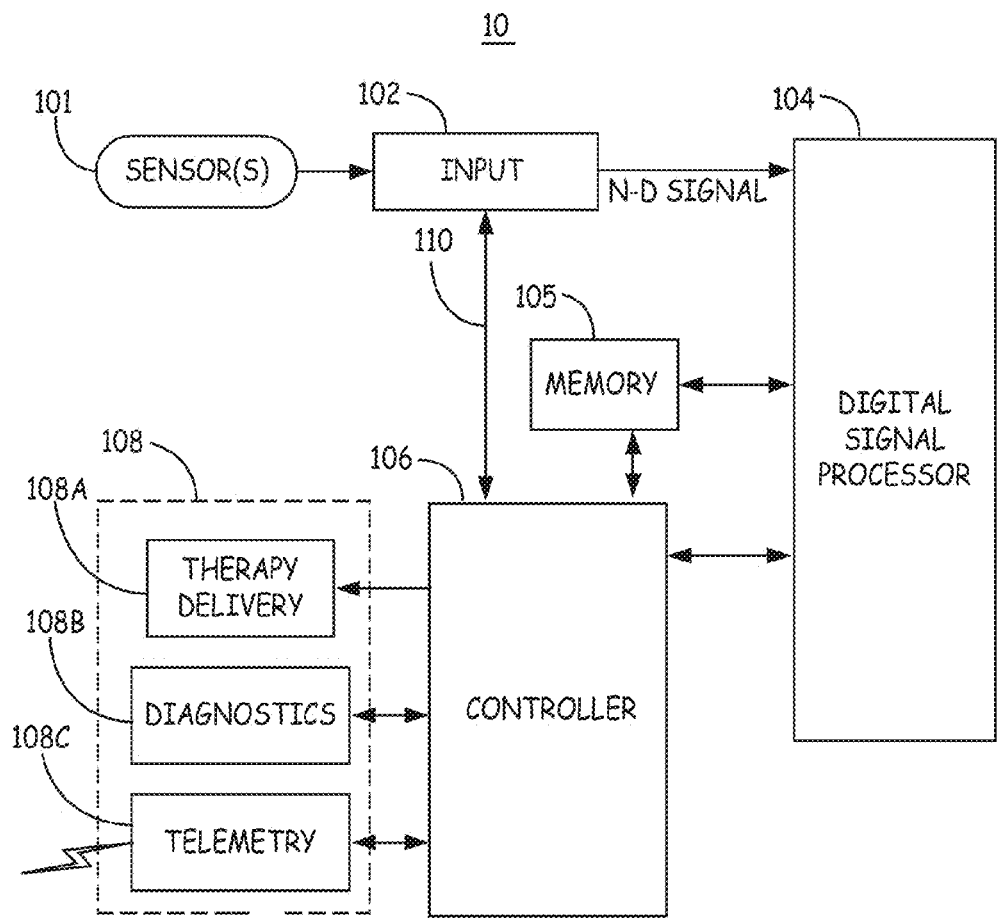
FIG. 3 is a functional block diagram of the IMD of FIG. 1.

FIG. 3 is a functional block diagram of IMD 10. IMD 10 includes a sensor module 101 including at least one physiological sensor, input module 102, digital signal processor (DSP) 104, memory 105, controller 106, and output module 108. Sensor module 101 may be a single sensor or any combination of sensors generating an n-dimensional signal responsive to physiological variables. Sensor module 101 may include an optical sensor 30 as described above generating an n-wavelength optical signal. Sensor module 101 may include additional sensors used by IMD 10 for detecting variable conditions and for use in detecting patient conditions and making therapy delivery decisions. Sensor module 101 may include an activity sensor, a posture sensor, ECG/EGM electrodes or other physiological sensors listed previously.

Input module 102 acquires sensor signal(s) when enabled for sensing by controller 106 by control/status line 110. Input module 102 may perform pre-processing signal conditioning, such as analog filtering. Input module 102 provides an n-dimensional signal to digital signal processor (DSP) module 104. Input module 102 may additionally provide other sensor signals to DSP module 104 and/or controller 106 for use in monitoring variable conditions and detecting a patient state.

DSP 104 receives the n-dimensional sensor signal and performs adaptive processing to provide a signal having a reduced dimensionality that can be used by controller 106 to monitor a patient condition and appropriately control output module 108. For an n-dimensional signal, up to n−1 dimensions can be eliminated based on PCA to allow the sensed signal response to a variable of interest to be analyzed for efficient and accurate detection of a patient condition. The adaptive processing performed by DSP 104, which includes PCA, computes the principal components of the n-dimensional signal variation under known variable conditions. PCA may be performed to compute the principal components of the signal data in response to one or more known conditions relating to a variable of interest. PCA may additionally or alternatively be performed to compute the principal components of the signal data in response to one or more known conditions for artifacts. Input from sensors 101 may be used to identify the variable conditions.

The results of PCA are stored in memory 105 and can be used to extract a signal having fewer than n dimensions but retaining significant variability of the signal response to a variable of interest for detecting a specific patient condition. This reduced dimensional signal may be obtained through artifact cancellation using principal components obtained for artifact conditions or by determining a match between a monitored n-dimensional signal with a first principal component template corresponding to the variable of interest under known conditions.

Controller 106 analyzes the digitally processed signal provided by DSP 104 to detect a patient condition using a detection algorithm which applies detection criteria to the received signal or metrics derived therefrom. Controller 106 may adaptively select artifacts to cancel based on results of the PCA. Controller 106 can also use the results of the processing by DSP 104 to selectively enable or disable sensors 101, or to select physiological signals processed by DSP 104. If any signal dimension is not contributing to the variation of the n-dimensional signal along a principal component, the value computed for that dimension in the principal component vector will be zero (e.g. a principal component axis defined by a vector of [x,y,0]). The sensor or signal corresponding to a signal dimension having a zero contribution to a principal component can be disabled by controller 106 or ignored during processing by DSP 104.

The sensor/signal selection can simplify the computations performed by DSP 104, thus reducing energy demands. In addition, the total amount of energy consumed is reduced by turning off those sensors that are providing signals high in artifact or signals that are merely redundant to signals received from other sensors or those required to manage a particular disease state.

The ability to adapt digital signal processing and the selection of sensor signals (and sensors) over time allows IMD 10 to accommodate situations in which artifact and signal characteristics change over time. By periodically repeating signal processing operations, DSP 104 provides data from which controller 106 can select signals or sensors to be used.

Controller 106 uses the digitally processed signals to make decisions regarding therapy delivery by therapy delivery module 108A, for storing patient data in diagnostics module 108B, and/or for transmitting data by telemetry module 108C. Controller 106 may employ a microprocessor and associated memory or digital state machines for timing sensing and therapy delivery functions and controlling other device operations in accordance with a programmed IMD operating mode.

Therapy delivery module 108A may provide electrical stimulation therapy or drug delivery therapy. In one embodiment, therapy delivery module 108A includes a pulse generator for generating low-voltage pacing pulses, e.g., for bradycardia pacing, cardiac resynchronization therapy, and anti-tachycardia pacing, and/or for generating high-voltage cardioversion/defibrillation shocks. Therapy delivery unit 108A includes therapy delivery elements (not shown) such as electrodes, catheters, drug delivery ports or the like for administering a therapy.

Diagnostics module 108B is used to store data relating to the analysis of digitally processed signals. Such data may be made available to a clinician via telemetry by telemetry module 108C or accessed by controller 106 for making therapy decisions. Diagnostics module 108B may perform analysis of multi-dimensional signal data plotted in an n-dimensional space to detect variation of signal data along principal components determined for known physiological conditions. When a pathological condition is detected that warrants medical attention, the controller 106 may cause telemetry module 108C to transmit a warning or alert to an external device or to a remote patient management database. A medical device system capable of generating an alert in response to detecting a patient condition is generally disclosed in U.S. Pat. Publication No. 2006/0064136 (Wang), hereby incorporated herein by reference in its entirety. A remote patient management system is generally disclosed in U.S. Pat. No. 6,497,655 (Linberg et al.), hereby incorporated herein by reference in its entirety.

Signal data may be additionally or alternatively transmitted to an external device or remote patient management database to allow plotting and display of multi-dimensional signal data in an n-dimensional coordinate system. Principal components for known physiological conditions may be superimposed on the plotted data to allow variation of the multi-dimensional signal along axes corresponding to known conditions to be recognized. By observing particular patterns in the signal data in n-dimensional space, a clinician may be able to diagnose or predict a particular patient condition and take appropriate action.

The signal acquisition, processing and analysis methods described herein may be implemented using any combination of software, hardware, and/or firmware in a dedicated module or across multiple modules within an IMD. Furthermore signal processing and analysis methods may be implemented across more than one device in a medical device system. For example, the signal acquisition may be performed by an implanted or an external device and at least a portion of the signal processing or analysis, including PCA, may be performed by another implanted or external device in telemetric communication with the signal acquisition device.

Figure 4:
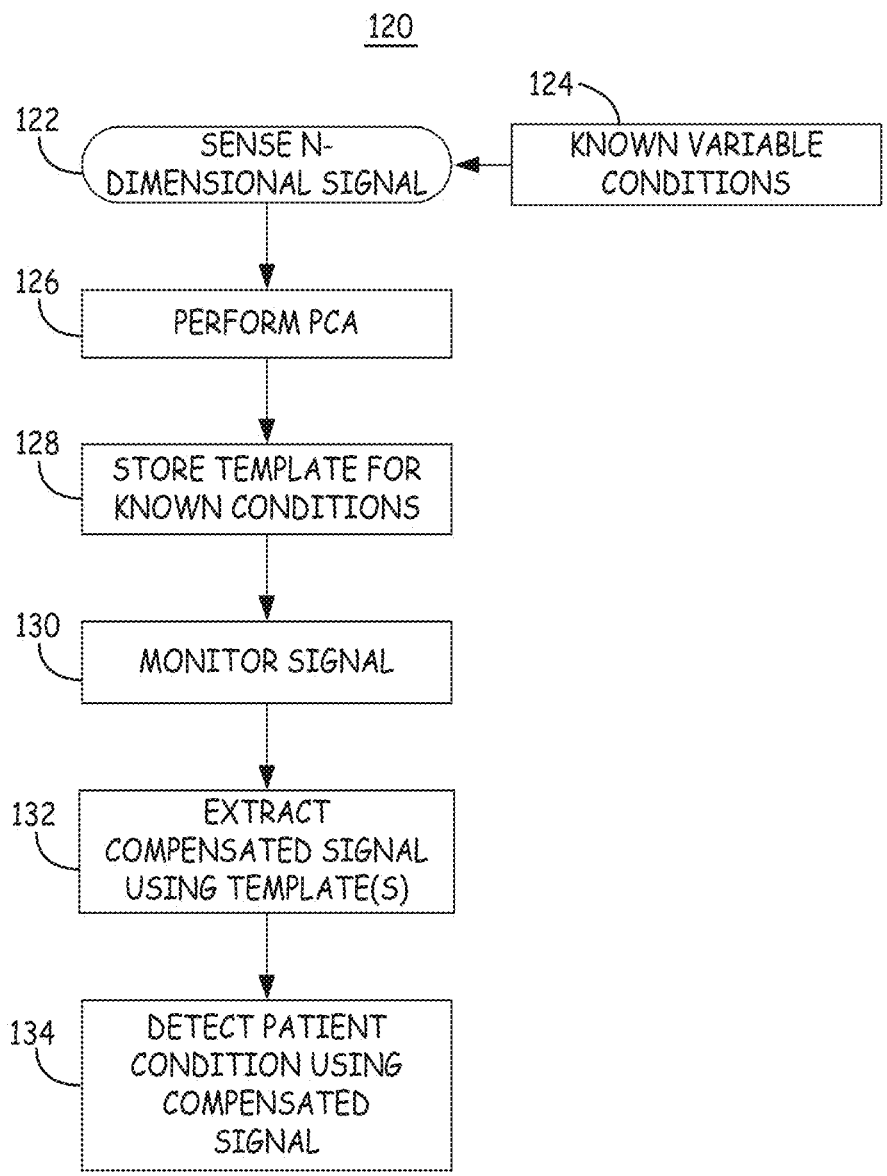
FIG. 4 is a flow chart of a method for detecting a patient condition using an n-dimensional physiological signal.

FIG. 4 is a flow chart of a method 120 for detecting a patient condition using an n-dimensional physiological signal. Flow chart 120 is intended to illustrate the functional operation of a medical device system, and should not be construed as reflective of a specific form of software, firmware or hardware necessary to practice the methods described. It is believed that the particular form of software, firmware or hardware will be determined primarily by the particular system architecture employed in the medical device system and by the particular sensing and therapy delivery methodologies employed by the medical device. Providing software, firmware and/or hardware to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 122, an n-dimensional signal is sensed under known variable conditions 124. PCA is performed on the sensed signal at block 126 to generate a template of the principal components of variation of the signal for the known variable conditions. One or more principal components are stored as a template of the signal data for the known conditions at block 128. Blocks 122 through 128 may be performed for multiple sets of known variable conditions to enable storage of multiple templates. Each template may include a single principal component, for example the first principal component or a principal component orthogonal to the first principal component. Alternatively, each template may include multiple principal components.

The known variable conditions identified at block 124 may correspond to a condition for a variable of interest to allow a template of the n-dimensional signal response for the variable of interest to be stored. The known variable conditions identified at block 124 may correspond to normal or pathological states of the variable of interest. For example, if the variable of interest is cardiac pulsatility, known variable conditions may correspond to normal sinus rhythm and one or more types of arrhythmias to allow templates for each type of heart rhythm to be stored. The storage of templates corresponding to a variable of interest allows features of an unknown signal to be analyzed using the stored template(s) for detecting a patient condition relating to the variable of interest.

Additionally or alternatively, the known variable conditions identified at block 124 may correspond to artifacts. One or more templates may be stored for known artifact conditions, such as body motion, to allow the template to be used to cancel the signal response corresponding to the artifact during signal analysis performed to detect a patient condition.

The known variable conditions may be identified by the medical device automatically at block 124, for example using other sensor signals such as an activity sensor, a posture sensor, ECG electrodes, etc. Alternatively, the known variable conditions may be identified manually and a user-entered command transmitted to the IMD via telemetry may indicate the presence of the known variable conditions.

At block 130, the n-dimensional signal is monitored during unknown variable conditions for detecting a patient condition. At block 132, one or more stored templates are used for extracting a signal from the n-dimensional monitoring signal that has fewer dimensions. The extracted signal will contain less variation due to artifact and retains significant variation due to a variable of interest. The extracted signal is thus compensated for artifact and is referred to generally herein as a "compensated signal". It is to be understood that the operations performed at block 132 may involve the use of multiple templates for determining a match between a template corresponding to a known variable condition and/or cancelling artifact.

At block 134, the medical device controller detects a patient condition in response to the compensated signal. Numerous detection algorithms may be applied at block 134 which may involve threshold comparisons, statistical analysis, neural networks or other methods for detecting a patient condition from the compensated signal. In response to a detected condition, the controller may make therapy delivery decisions, store patient data, or initiate telemetric communication with another device.

Figure 5:
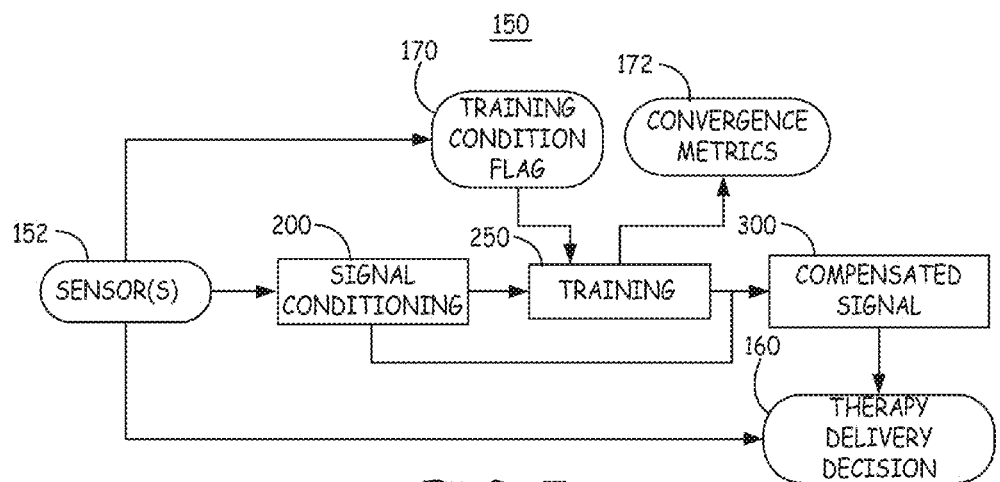
FIG. 5 is a functional block diagram of a signal processing module implemented in a medical device to perform the signal processing and analysis methods used in the method of FIG. 4.

FIG. 5 is a high-level functional block diagram of a signal processing module 150 implemented in a medical device to perform the signal processing and analysis method 120 of FIG. 4. A signal conditioning module 200 receives input from sensor(s) 152. Input from sensor(s) 152 includes an n-dimensional sensor signal. In illustrative examples described herein, a multi-wavelength optical sensor signal is provided by sensor(s) 152. It is contemplated that any multi-dimensional signal may be analyzed according to the methods described herein. Other sensor signals may be provided by sensors 152 for monitoring variable conditions and for use in making therapy delivery decisions or storing diagnostic data.

Signal conditioning is performed by signal conditioning module 200 to provide a digital, time-varying n-dimensional signal to training module 250. Additional details regarding signal conditioning performed by module 200 will be described below in conjunction with FIG. 6.

Training module 250 determines and stores templates of principal components of variation of the n-dimensional signal in response to the variable of interest and/or artifacts under known variable conditions. Training is performed during selected intervals of time as indicated by training flag 170. Training intervals can be determined automatically using signals from sensor(s) 152 or manually identified by a patient or clinician when variable conditions are known, for example periods of a known cardiac rhythm, a known patient activity or activity level, a known patient posture, etc. During training, a principal component of the multi-dimensional signal is computed and updated using an incoming stream of signal data from signal conditioning module 200.

A convergence metric 172 may be computed using data provided by the training module 250. The convergence metric 172 may be updated as the principal component is updated in response to incoming streaming data. The convergence metric is used by the medical device controller to determine when the principal component computed by training module 250 has reached a "steady-state" for the known variable conditions. The convergence metric is used to determine when the variation in direction of the incoming n-dimensional data is occurring within an acceptable range so that the currently computed principal component is a reliable representation of that variation. The principal component is stored as a template of the signal response to the known variable condition(s) when the convergence metric indicates the signal data has converged within an acceptable range of variation.

As indicated above, the template may include one or more principal components which may include the first principal component of the signal data and/or one or more principal components orthogonal to the first principal component. Additional details regarding the operations performed by training module 250 will be described below in conjunction with FIG. 7.

A compensated signal module 300 receives a conditioned sensor signal from signal conditioning module 200, referred to as the monitoring signal. The monitoring signal is received by compensated signal module 300 during unknown variable conditions for monitoring the patient and detecting a patient condition. In some embodiments, compensated signal module 300 also receives the monitoring signal during known variable conditions when the training module 250 is determining and storing a principal component. For example, as will be described below, the compensated signal module 300 provides data for determining convergence metrics for terminating a training interval. In other embodiments, signal processing module 150 operates in a training mode during training intervals of time identified by training flag 170 and operates in a monitoring mode during other intervals of time when training flag 170 is not present. When a training flag 170 is present indicating known variable conditions, training module 250 is enabled to perform PCA to generate and store a template.

When a training flag 170 is not present, signal processing module 150 may be enabled by the medical device controller to monitor the n-dimensional signal for detecting a patient condition. During monitoring, one or more stored principal component templates provided by training module 250 are used by compensated signal module 300 to convert the monitoring signal received from signal conditioning module 200 to a compensated signal.

The incoming monitored sensor signal from signal conditioning module 200 may be thought of as an "uncompensated" signal in that it represents the signal data before adjustment of the data has been performed using the results of PCA. A compensated signal is computed by module 300 to adjust the monitoring signal using one or more principal component templates to extract a signal having fewer dimensions than the original n-dimensional signal.

A compensated signal may represent the match or goodness of fit between the monitored incoming signal and a principal component of a variable of interest during known conditions. In this way, the compensated signal computed at block 300 can be thought of as a signal reflecting how well the monitoring signal matches a known variable condition. The compensated signal computed by module 300 may alternatively or additionally represent the monitored incoming signal with artifact cancellation. In this case, the compensated signal represents the variation of the monitoring signal primarily due to the variable(s) of interest with the influence of one or more artifacts removed. Additional details regarding the operations of compensated signal module 300 will be described below in conjunction with FIG. 10.

The compensated signal is used by therapy delivery decision block 160 to make therapy decisions. Other input from sensors 152 may be used in making therapy decisions. Therapy decisions may include initiating a therapy, canceling or aborting a therapy, or adjusting an ongoing therapy. In the example of IMD 10 shown in FIG. 1, the IMD controller may detect ventricular fibrillation based on ECG signals sensed using electrodes coupled to IMD 10. Upon detecting fibrillation, a compensated reflectance signal derived from a multi-wavelength optical sensor is used as input to therapy delivery decision block 160 to confirm the VF detection and make therapy delivery decisions.

Figure 6:
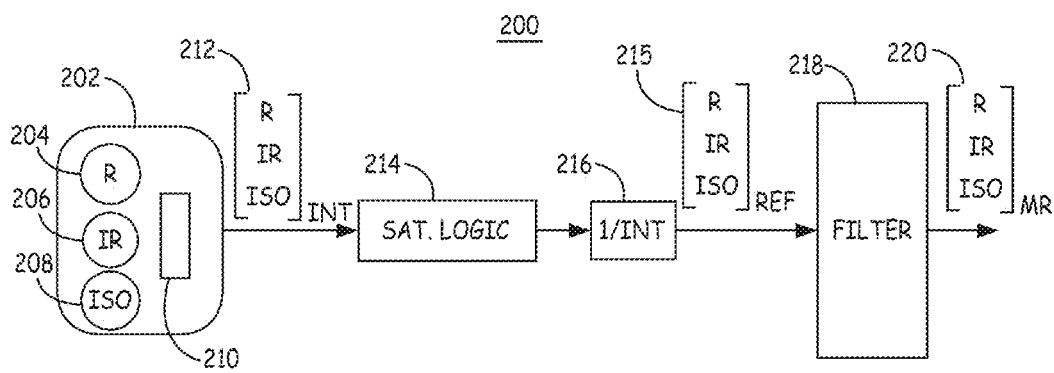
FIG. 6 is a schematic diagram of an optical sensor and the signal conditioning module of FIG. 5.

FIG. 6 is a schematic diagram of an optical sensor and the signal conditioning module 200 of FIG. 5. Signal conditioning module 200 is used to provide an n-dimensional signal to the training module 250 of FIG. 5 for computing and storing signal templates. Signal conditioning module 200 is further used to provide an n-dimensional, monitoring signal to compensated signal module 300 of FIG. 5.

Sensor 202 is shown as an optical sensor including emitters 204, 206, and 208 each emitting light signals centered at different wavelengths. For example, a red (R) signal, an infrared (IR) signal, and an isobestic (Iso) signal may be provided. A detector 210 receives light scattered by blood and tissue adjacent sensor 202. The received light can include ambient light and scattered light corresponding to each of the three emitted light wavelengths. Sensor 202 provides time intervals for each of the three wavelengths detected by detector 210. As described above, the time intervals are determined as the time for an integrated light signal to reach a predetermined magnitude.

The time intervals for the three wavelengths can be considered a three dimensional signal. Each 3-dimensional signal value can be thought of as a column matrix 212. Column matrix 212 represents the interval measurements for each of the three wavelengths at a given sample time. Column matrix 212 has three rows, i.e., a 1×3 matrix, with each row representing a time interval measurement (INT) for one of the three wavelengths. In one embodiment, a column matrix is filled as interval measurements are made for each of the three wavelengths using a single broadband light detector. This approach provides a time-divided multiplexed three-dimensional signal using a single photodetector. In other embodiments separate narrow-band light detectors could be provided in an optical sensor for generating amplitude or time interval measurements for separate wavelengths which could then be multiplexed to form an n-dimensional signal. While sensor 202 is described as an optical sensor producing a three-dimensional signal, it is recognized that methods described herein may be applied to any optical signal including two or more wavelengths.

Furthermore, signal conditioning module 200 may be adapted to receive any of the n-dimensional sensor signals described above including, but not limited to, an acoustical signal having multiple frequency dimensions, a motion signal having multiple dimensions in space, and an ECG signal sensed using multiple sensing vectors. Signal conditioning operations performed by module 200 will vary depending on the type of multi-dimensional signal received.

Saturation logic 214 is provided in one implementation to maintain the optical signal interval measurements within a logical range of minimum and maximum values to prevent mathematical errors, such as divide by zero errors. For example, if an interval in column matrix 212 is less than 0.1 ms, saturation logic 214 sets the interval to 0.1 ms. If the interval is greater than 1000 ms, saturation logic 214 sets the interval to 1000 ms.

In addition to saturation logic 214, a dark interval correction block (not shown) could optionally be included to correct for baseline offset due to current leakage within the optical sensor electronics that occurs in the absence of light. Correction for the dark interval for a given sensor can be made based on the measured dark interval for the sensor, for example during manufacturing and device testing processes. If the dark interval exceeds a desired threshold, offset correction may be included in signal conditioning module 200 to subtract the offset from the incoming signal data.

Block 216 is an inverter that converts each time interval to a reflectance. A 1×3 matrix of reflectance measurements (REF) 215 is provided as input to filter 218. Filter 218 performs filtering operations to remove the mean from the each of the reflectance measurements and optionally remove high-frequency, non-physiological noise. In order to perform PCA, the individual means for each dimension of the signal are removed so that the overall signal data has a mean of zero. Referring to the three-dimensional coordinate system 80 of FIG. 2, the mean-removed data will have a baseline centered on the origin of the coordinate system. This allows the principal components to be computed as vectors extending from an origin of coordinate system to a point computed using PCA.

Filtering performed by filter 218 may be implemented in any combination of parallel or staged filters for obtaining the mean-removed (MR) and noise filtered output signal 220. During monitoring modes of operation, the mean-removed signal 220 is the monitoring signal received by compensated signal module 300 of FIG. 5. During training modes of operation, the mean-removed signal 220 is the signal used by the training module 250 of FIG. 5 for computing a principal component template during known variable conditions. Mean-removed signal 220 may be provided to the training module 250 and the compensated signal module 300 simultaneously or at separate times.

Filter 218 may include a low pass filter to produce a mean DC signal. The mean signal represents a relatively "long term" mean of reflectance measurements for each of the three wavelengths. For example, the mean signal may represent the mean reflectance for each of the wavelengths over 2 seconds or longer. In one embodiment, the mean signal is obtained by applying a low pass filter having a pass band of approximately 0 to 0.5 Hz. In alternative embodiments, mean values for each signal dimension may be determined from buffered signal values, for example 20 buffered samples or any other desired number of samples, to compute a mean DC signal.

Filter 218 may further include a low pass filter having a wider pass band, for example approximately 0 to 10 Hz or 0 to 100 Hz, for removing high-frequency noise. The cut-off frequency of this low pass filter can be selected to remove frequencies that are considered non-physiologic. The mean DC signal may then be subtracted from the noise-removed signal to obtain the mean-removed output signal 220.

Alternatively, filter 218 may include a bandpass filter for filtering the incoming reflectance signal 215 to remove the means for each of the individual wavelengths and any high frequency non-physiologic noise. For example, a 0.5 to 10 Hz or 0.5 to 100 Hz bandpass filter may be used to provide the mean-removed output signal 220. It is recognized that this frequency range and other filter frequency ranges specified herein are merely examples of ranges that might be used and the actual filtering characteristics will be selected and optimized for a particular medical device application.

Mean-removed output signal 220 is referred to as an "uncompensated" signal in that the 1×3 matrix represents the monitoring signal before compensation using stored principal component templates. A "compensated" signal, as described above, is computed using the mean-removed signal 220 and a principal component template to adjust the monitoring signal based on PCA results.

Figure 7:
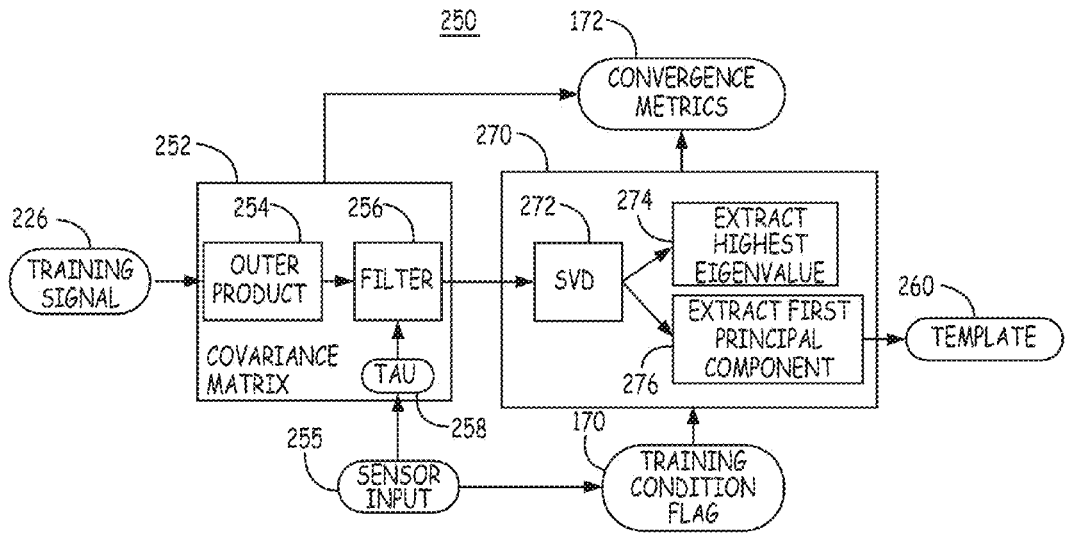
FIG. 7 is a functional block diagram of a training module used for computing principal component templates from a sensor signal.

FIG. 7 is a functional block diagram of a training module used for computing principal component templates from a mean-removed sensor signal. In PCA, a principal component of an n-dimensional signal response to known variable conditions is computed from a covariance matrix of the individual signal dimensions. Using the example of a multi-wavelength reflectance signal, the principal component of the n-wavelength reflectance signal is computed using the covariance matrix of the reflectance measurements for the n wavelengths.

Prior to computing the covariance matrix, the mean reflectance is subtracted from the reflectance measurements for each wavelength, e.g. by filter 218 of FIG. 6. By subtracting the means, the data will have a mean of zero which will center a principal component coordinate system at the origin as shown by the example in FIG. 2. The mean-removed training signal (output of signal conditioning module 200) is used to compute a covariance matrix. Using a two-wavelength reflectance signal as an example, a training signal X is provided as a mean-removed signal, e.g., a bandpass filtered output of signal conditioning module 200, which can be expressed as a 1×2 matrix:

$$X = \begin{bmatrix} R - \overline{R} \\ IR - \overline{IR} \end{bmatrix} = \begin{bmatrix} R \\ IR \end{bmatrix}_{MR}$$

The mean-removed training signal may be acquired through digital filtering as described above. Alternatively, the mean-removed signal may be computed mathematically by subtracting a mean reflectance from the individual reflectance measurements for each wavelength. A mean reflectance may be a running mean computed from a desired number of reflectance measurements or measurements acquired over a desired interval of time.

In FIG. 7, the training signal 226 is provided as input to covariance matrix module 252. In covariance matrix module 252, an outer product block 254 computes the covariance matrix of the training signal. Since the signal means have already been subtracted from the data, the covariance matrix can be computed using the outer product of the training signal matrix X and its transpose:

$$cov[X] = \text{mean}([X][X]^T)$$

Computation of the covariance matrix can be shown mathematically as:

$$\text{mean}\left(\begin{bmatrix} R \\ IR \end{bmatrix} \otimes [R \ IR]\right) = \text{mean}\left(\begin{bmatrix} R*R & R*IR \\ IR*R & IR*IR \end{bmatrix}\right)$$

The main diagonal of the covariance matrix corresponds to the variances of the individual signal dimensions. The upper left value corresponds to the variance of the red reflectance signal and the lower right value corresponds to the variance of the infrared reflectance signal. The covariance matrix is symmetrical about the main diagonal since cov(IR,R) is equal to cov(R,IR). While a 2×2 covariance matrix computed from a 1×2 signal is shown, it is to be understood that the training signal may be any 1×n signal matrix corresponding to an n-dimensional sensor signal. The resulting covariance matrix is an n×n covariance matrix.

In one embodiment, the covariance matrix is filtered at block 256, which may be a first order lowpass filter. Each individual element of the covariance matrix is filtered using a filter time constant, tau, 258. The filter time constant 258 is selected according to an expected frequency of the variable of interest or the artifact for which the template is being generated, thus providing a cleaner signal from which the template will be computed. For example, if the principal component for a cardiac variable is desired during normal sinus rhythm, the time constant 258 may be set to allow the covariance matrix to be filtered with a frequency that retains signal variations that occur with the cardiac variable, e.g. at a frequency centered around approximately 1 Hz, and filters variations that occur at other frequencies due to artifacts such as respiration or body motion. If the principal component for respiration artifact is desired for use in artifact cancellation, the time constant 258 may be set to be long enough to retain signal variations that occur at the expected frequency of the patient's respiration and filter other frequency variation such as cardiac pulsatility variations. If the principal component for body motion variation is desired, the time constant 258 may be set to retain the frequency of the body motion signal, e.g. derived from an activity sensor, and filter other signal variation frequencies. The selection of the time constant 258 can be thought of as setting a window of time over which a filtered covariance matrix is generated from a stream of computed covariance matrices. As such, time constant 258 is inversely related to the frequency of the variable for which the principal component is being computed.

The time constant 258 may be selected based on input from other sensors 255. For example, a respiration signal, an activity signal, or other sensor signal input may be received by the medical device controller to select the appropriate time constant 258 to be inversely proportional to the frequency of the variable condition for which the principal component is being computed. In one embodiment, when filtering a respiration artifact signal, the time constant 258 may be set using input from an activity sensor such that the time constant 258 is set to a shorter time interval when activity is high and the respiration rate is expected to be high. Similarly, time constant 258 is set to a relatively longer time interval when activity is low and the respiration rate is expected to be low.

Using the filtered covariance matrix, PCA module 270 computes the principle components of the covariance matrix. PCA module 270 is enabled in response to training condition flag 170 which indicates a state of known variable conditions is detected. Flag 170 may be generated automatically by the medical device controller in response to input from other sensors 255 or in response to a user-entered command.

PCA module 270 includes a singular value decomposition (SVD) block 272. SVD block 272 performs a factorization operation on the covariance matrix received from covariance matrix module 252 to determine a matrix of eigenvectors and the eigenvalue matrix for the covariance matrix. For an n×n covariance matrix, an n×n eigenvector matrix is derived which includes n eigenvectors in the columns of the matrix. The n eigenvectors are orthogonal unit vectors extending from the origin of the n-dimensional coordinate system and represent patterns of the multi-dimensional data. In particular, one column of the eigenvector matrix corresponding to the greatest eigenvalue will be a vector defining an axis along which the greatest variation of the signal data occurs for the current variable conditions, i.e., the first principal component.

The eigenvalue matrix is an n×n diagonal matrix containing the squares of the eigenvalues for the eigenvectors along its diagonal. The eigenvalue matrix column containing the highest eigenvalue indicates the most significant relationship between the signal dimensions. The largest eigenvalue can thus be used to identify the eigenvector defining the first principal component of the signal data for the known variable conditions. When n-dimensional signal data is acquired, the eigenvectors corresponding to the highest eigenvalues may be selected and other eigenvectors, associated with the least significant variation of the signal data, may be ignored, allowing the number of dimensions to be reduced in an analysis of the data.

At block 274, the greatest eigenvalue is extracted. At block 276, the column of the eigenvector matrix corresponding to the column in which the greatest eigenvalue is present is extracted as the first principal component of the signal data. Other signal components defined by the other eigenvectors may be ignored. In alternative embodiments, two or more eigenvectors may be extracted at block 276 based on identifying the highest eigenvalues.

The greatest eigenvalue may be required to be greater than other eigenvalues by a predetermined amount in order to extract a first principal component. For example, the greatest eigenvalue may be required to be at least 10 times greater than other eigenvalues in order to accept the corresponding eigenvector as the first principal component and ignore all other principal components. If no eigenvalues reach criteria for selecting a first principal component, no template is stored for the current variable conditions.

The output of PCA module 254 is the derived first principal component of the signal data which is stored as a template 260 for the known variable conditions. In other words, the principal component template 260 defines an axis extending through the n-dimensional coordinate system along which the greatest variation of the multi-dimensional signal occurs in response to the known variable conditions.

While extraction block 276 indicates only the first principal component is extracted, it is to be understood that other principal components may be extracted in addition to or alternatively to the first principal component. Thus the template 256 may represent multiple principal components for the known variable conditions or a single principal component, which may be the first principal component or a principal component orthogonal to the first principal component.

In one embodiment, convergence metrics 172 are computed during the training mode to determine when a principal component template 260 can be stored based on the convergence of the training signal data. One or more convergence metrics 172 may be provided by covariance matrix module 252 and/or PCA module 270. In one embodiment, the variances of the individual signal dimensions (along the main diagonal of the covariance matrix) may be provided by outer product block 254 to be used as convergence metrics. For example, the variance of red or infrared reflectance signals and/or covariances of these signal dimensions may be compared to an acceptable range. Once the convergence metric(s) remain within an acceptable range, the first principal component (or other principal component) extracted at block 276 is stored as the template 260 for the currently known variable conditions.

In another embodiment, the highest eigenvalue extracted at block 274 may be provided to the medical device controller for use as a convergence metric. One or more convergence metrics may be computed or derived from any of the eigenvalues or eigenvectors computed by SVD block 272. The medical device controller determines when the convergence metric(s) 172 have reached a steady state, i.e., vary within an acceptable range. Upon detecting convergence, the template 260 is stored for the known variable conditions.

Training module 250 may be implemented to respond to training flag 170 for acquiring a template corresponding to a variety of known variable conditions. Variable conditions may relate to multiple states for a given variable, or to different combinations of variables. For example, a template may be stored for normal sinus rhythm at rest, normal sinus rhythm at different activity levels (e.g., low, moderate and high levels of exertion) or different types of activity (e.g., walking, climbing stairs, etc.), different body postures, and during known arrhythmias such as VT, VF or atrial tachycardias. As long as training condition flag 170 is active or high, the training module operates to derive the principal components of the training signal until convergence criteria are satisfied and the template is stored. If the training condition flag 170 is inactive or low before the controller determines that convergence has been reached based on the convergence metrics 172, PCA module 270 may terminate computation of the principal components of the signal data without storing a template. A training flag 170 may be removed before template storage is complete due to detection of a change in the known variable conditions based on sensor input or a user-entered command.

In some embodiments, updating of principal component templates may be performed in response to detecting a change in patient conditions. For example, a training flag may be set in response to determining that the patient is at rest. The training module 250 responds by computing a principal component from streaming data corresponding to the resting condition of the patient. When the patient activity changes, the training flag may be removed to allow the computed principal component to be stored for the resting condition. The training flag may then be reset to allow the principal component to be updated for the new level of patient activity until a change in activity is detected again. As such, a training flag may be set, removed and reset based in response to a physiological signal to control the times at which computation of a principal component from streaming data is initiated and when computed principal component values are locked in and stored as a template. In another embodiment, principal component computation may operate continuously with the training flag, and optionally convergence metrics, indicating when component values should be stored based on detected variable conditions.

Figure 8:
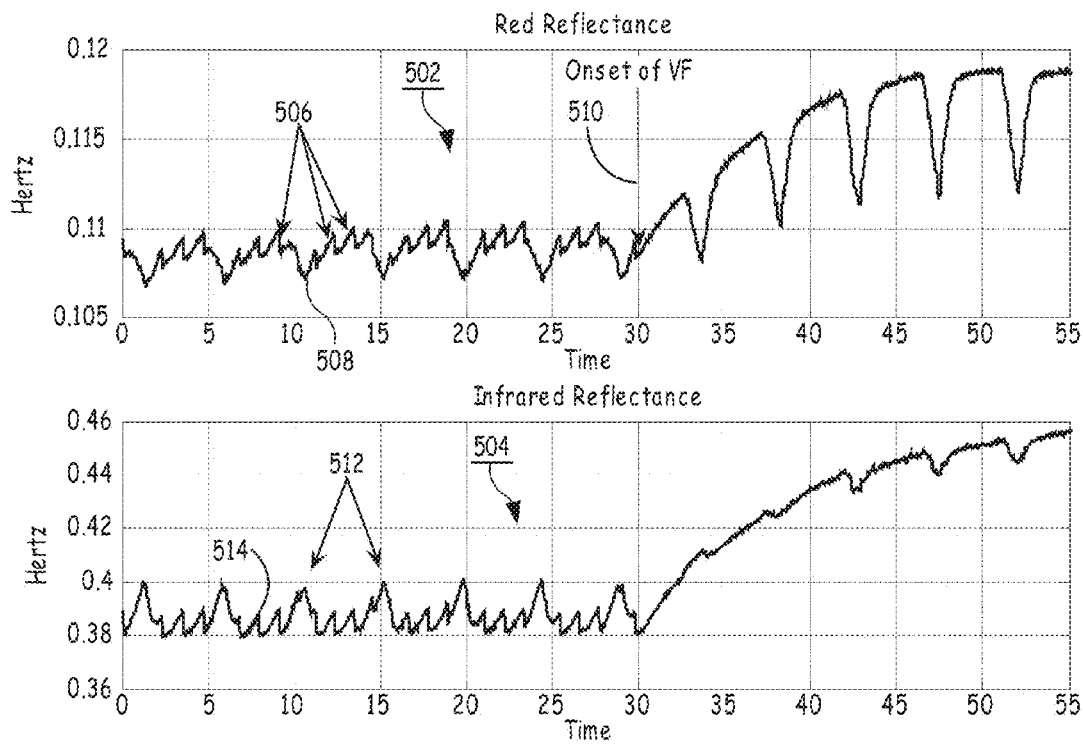
FIG. 8 shows a recording of a time-varying two-dimensional reflectance signal.

FIG. 8 shows a recording of a time-varying two-dimensional reflectance signal. The top panel is the R reflectance 502 and the bottom panel is the IR reflectance 504. The response of the R reflectance 502 to cardiac pulsatility during normal sinus rhythm is observed as positive going peaks 506. The negative-going peaks 508 correspond to the response of the R reflectance 502 to ventilator artifact. The response of the IR reflectance signal 504 to ventilator artifact is seen as positive-going peaks 512. Smaller positive-going peaks 514 correspond to the response of the IR reflectance signal 504 to cardiac pulsatility during normal sinus rhythm.

The onset of VF occurs at 510. The R reflectance 502 and IR reflectance 504 are both observed to increase in amplitude and the variation corresponding to cardiac pulsatility on the signals disappears.

Figure 9:
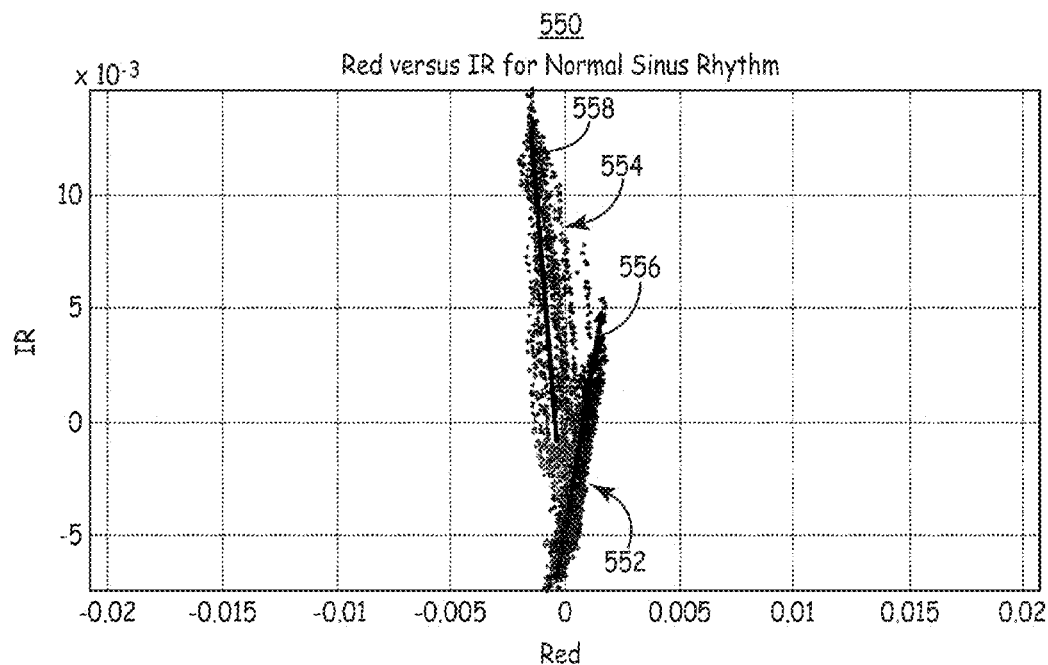
FIG. 9 is a plot of the mean-removed, two-dimensional reflectance signal of FIG. 8 during known variable conditions.

FIG. 9 is a plot of the mean-removed two-dimensional reflectance signal of FIG. 8 during the known variable conditions. The signal data is plotted in a two-dimensional coordinate system in which the R reflectance values are plotted along the x-axis and the IR reflectance values are plotted along the y-axis. A first clustered set of data points 552 represents normal sinus rhythm with ventilator artifact removed. The second set of clustered data points 554 represents normal sinus rhythm with ventilator artifact present. The two different variable conditions are seen to result in two different patterns in the signal data.

The covariance matrix for the mean-removed data set 552 (normal sinus rhythm with no ventilator artifact) is:

|    | R | IR |
|----|---|----|
| R  | $0.0193*10^{-5}$ | $0.1113*10^{-5}$ |
| IR | $0.1113*10^{-5}$ | $0.6971*10^{-5}$ |

The variance of the IR reflectance is seen to be more than one order of magnitude greater than the variance of the R reflectance. This is observed by the greater variation of the data along the y-axis than along the x-axis in FIG. 8.

PCA performed on the mean-removed data set 552 produces a first principal component 556. The eigenvector matrix derived by performing SVD on the covariance matrix is approximately:

$$\begin{pmatrix} -0.99 & 0.16 \\ 0.16 & 0.99 \end{pmatrix}$$

The eigenvector for the first column is a unit vector extending from the coordinate system origin to the point (−0.99, 0.16). The eigenvector for the second column is a unit vector extending from the origin to the point (0.16, 0.99). These eigenvectors are orthogonal vectors defining the principal components of variation of the data set 552.

The eigenvalue matrix derived from SVD of the covariance matrix given above is approximately:

$$\begin{pmatrix} 0.002 \times 10^{-5} & 0 \\ 0 & 0.72 \times 10^{-5} \end{pmatrix}$$

The second column clearly contains the highest eigenvalue. Accordingly, the first principal component of the signal data is found in the second column of the eigenvector matrix. In FIG. 9, this first principal component 556 defined by the second column eigenvector having the highest eigenvalue is shown extending through the coordinate system origin and along an axis of greatest variability of the signal data. The first principal component 556 thus represents an axis extending through the 2-dimensional coordinate system along which the signal data is expected to have the greatest variation during normal sinus rhythm with no ventilator artifact. The set of data points 552 is seen to be substantially symmetric around the first principal component 556.

The first column of the eigenvector matrix defines a vector corresponding to the second principal component that would extend orthogonally to the first principal component through the 2-dimensional coordinate system. However, this second principal component can be ignored in this example since more than 99% of the signal data variation occurs along the first principal component during normal sinus rhythm with no ventilator artifact.

A similar analysis of the mean-removed data set 554 produces a first principal component 558. First principal component 558 is defined by the eigenvector extending through the origin and along the axis of greatest signal variability during normal sinus rhythm with ventilator artifact present. Under these variable conditions, first principal component 558 represents the axis along which the 2-dimensional signal is expected to vary.

As will be further described below, these first principal components 556 and 558 can be stored as templates for the known variable conditions and used in identifying patient conditions corresponding to unknown signal data. For example, comparisons to the first principal component 556 for normal sinus rhythm can be used to detect a cardiac rhythm condition. The template 260 stored in FIG. 7 for known variable conditions may include one or more of the orthogonal principal components. In some embodiments, only the first principal component is stored and other principal components are ignored. In other embodiments, orthogonal principal components may be stored if high eigenvalues indicate a large variation of the data in the direction of other principal components. In still other embodiments, principal components orthogonal to the first principal component may be stored for use in canceling artifact as will be described below in conjunction with FIGS. 10 and 11. For example, a principal component vector orthogonal to the ventilator artifact first principal component 558 can be used to cancel ventilator artifact in a monitoring signal during unknown variable conditions.

Figure 10:
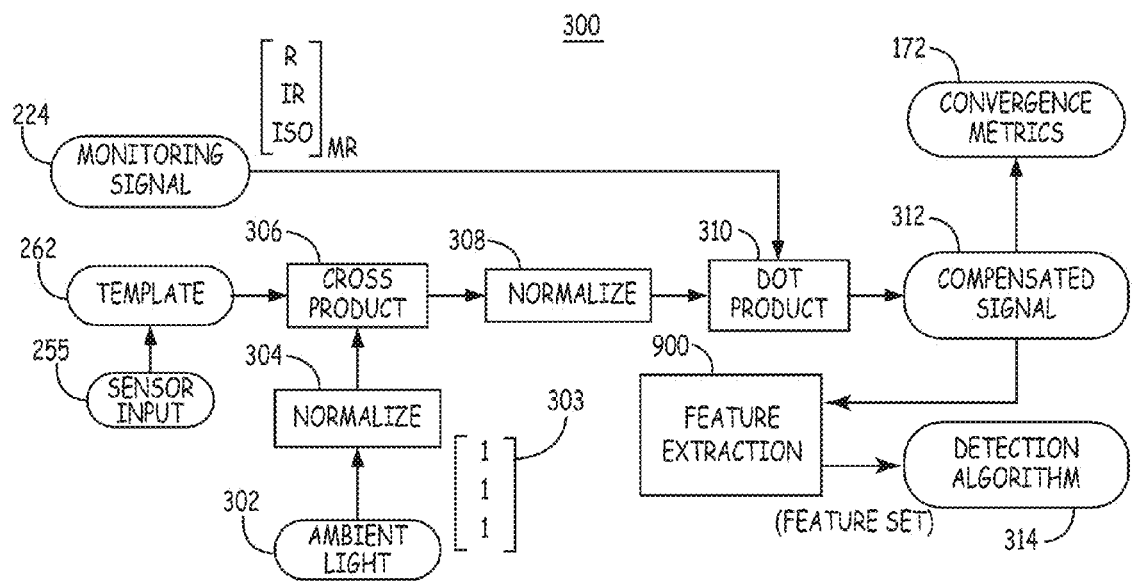
FIG. 10 is a functional block diagram of the compensated signal module of FIG. 5.

FIG. 10 is a functional block diagram of compensated signal module 300 of FIG. 5. During a monitoring mode of operation, the signal processing module 150 of FIG. 5 monitors the mean-removed signal output of signal conditioning module 200 (FIG. 6) to detect a patient condition. The output of signal processing conditioning module 200 is provided as a monitoring signal 224 to compensated signal module 300. As mentioned previously, a compensated signal is a signal computed using the monitoring signal 224 and a stored template 262.

A template 262 used for computing the compensated signal may be selected based on the patient condition being monitored. For example, if the n-dimensional sensor signal is to be used for verifying VF detection, the template 262 may be selected as the template corresponding to the first principal component of the signal data during normal sinus rhythm conditions. Artifact directions in FIG. 10 may consist of a sinus rhythm template 262 and an ambient light template 302. The result of the normalized cross product (from block 308) defines a direction of interest for the monitoring signal 224 that has nulled out or removed these two artifacts. The compensated signal may provide a comparison of the monitoring signal 224 and the template.

Alternatively, template direction(s) may be selected according to signals of interest. For example, the input for the dot product 310 may be a prominent direction contained in the signal of interest. Thus a template may be a first principal component or one of the principal components orthogonal to the first principal component. When a principal component orthogonal to the first principal component of the signal data during a known artifact condition is used to compute a compensated signal, the artifact condition is cancelled from the compensated signal.

The template 262 provided to compensated signal module 300 may be selected based on other sensor input 255. For example, sensor input 255 may include patient activity, posture, respiration, ECG or other information that allows an appropriate template 262 to be selected for the current variable conditions. In the case of monitoring a patient cardiac rhythm for verifying a VT detected using ECG signals, the medical device controller may check the patient activity and/or posture to select a template that was acquired during similar patient activity or posture. For example, if the activity signal indicates the patient is climbing stairs, template 262 is selected as the template stored during similar activity conditions to allow the body motion artifact to be cancelled in the compensated signal.

Initially, template 262 may be corrected for ambient light contributions 302 when the n-dimension signal is an optical signal. Since ambient light is generally white light, affecting all light wavelengths, an ambient light compensation matrix 303 is a 1×n matrix in which each value in the matrix is 1. The ambient light compensation matrix is normalized at block 304 using the magnitude of the ambient light vector to produce a unit vector. Alternatively, the ambient light compensation matrix 303 may already be stored as a normalized, unit vector reducing the computational steps required for correcting the template for ambient light.

In an alternative embodiment, ambient light may be measured directly by measuring the optical signal when the light emitting portion of the optical sensor is not emitting light. An ambient light signal may then be provided as a three-dimensional column vector. The ambient light vector may be normalized by the vector magnitude to provide an ambient light compensation vector as a unit vector.

At block 306, the cross product of the normalized, ambient light compensation vector and the template 262, such as a template associated with sinus rhythm artifact, for example, is computed. The cross-product operation provides a vector orthogonal to both the ambient light vector and the sinus rhythm vector, i.e. with the ambient light and sinus rhythm contributions removed. The sinus rhythm artifact template is thus corrected for the ambient light. The ambient light correction operations are optional and may be used depending on the susceptibility of the optical sensor to ambient light. In some applications, the optical sensor may be implanted deep within tissue and not be susceptible to ambient light. In other applications, an optical sensor may be just beneath the skin and be susceptible to ambient light, which can fluctuate throughout the day.

In other embodiments which utilize other types of n-dimensional sensor signals, other noise correction operations may be performed on a selected template 262 to correct for noise present at the time the monitoring signal 224 is acquired.

At block 308, the corrected template is normalized by the magnitude of the corrected template to be a unit vector. In some embodiments, this normalization block 308 is not required if the template has already been normalized by training module 250. The results of singular value decomposition software are typically provided as normalized eigenvectors, making normalization block 308 unnecessary.

The normalized, corrected template and the monitoring signal are provided as input to block 310. Generally, block 310 computes a compensated signal 312 using the normalized corrected template and the monitoring signal. The compensated signal 312 is used by the medical device controller for detecting a patient condition at block 314, or as described previously for making a therapy delivery decision at block 160 of FIG. 5.

In one embodiment, block 310 computes a dot or inner product of the normalized corrected template and the monitoring signal 224. The dot product is a scalar output and thus block 310 reduces the n-dimensional signal to a one-dimensional signal. For example, the dot product operation performed at block 310 may be the dot product of the corrected, normalized template representing the first principal component for a known variable condition and the monitoring signal. The resulting one-dimensional signal will represent the match between the template and the monitoring signal. The dot product will be zero when the two vectors (i.e., the template and the monitoring signal at a sample time point) are orthogonal and will approach the amplitude of the monitoring signal when the two vectors are in close alignment.

Alternatively, the dot product operation performed at block 310 may be the dot product of the monitoring signal and a principal component template orthogonal to one or more principal components for an artifact condition. Since the dot product of two orthogonal vectors is zero, artifact and ambient light can be removed from the monitoring signal in the resulting compensated signal 312. The dot product will represent the effect of removing the first principal component of the artifact from the incoming monitoring signal. This approach may be used for canceling artifact in the monitoring signal. For example, if cancellation of body motion artifact is desired, the dot product computed at block 310 may be computed using the monitoring signal and a principal component template orthogonal to the first principal component determined for a known condition for body motion. The compensated signal 312 will then represent the monitoring signal with the body motion artifact removed (and ambient light cancelled), allowing analysis of the compensated signal for detecting a patient condition associated with the variable of interest.

In some embodiments, the compensated signal is computed from the streaming data simultaneously during computation of a template by the training module 250 of FIG. 7 and provided for computing a convergence metric 172. A convergence metric 172 may be a comparison of the variance of the compensated signal to the variance of individual wavelengths received by the training module 250. When the variance of the convergence metric is within predetermined limits as compared to the variances of the individual wavelengths, the controller may cause the training module 250 to store the currently computed template for the existing variable conditions. The training module 250 stops computing the template, and compensated signal module 300 continues to compute compensated signal 312 using the stored template.

A set of features are extracted from the compensated signal 312 for use in verifying a detected event, such as VF for example. One or more features may be extracted from the compensated signal 900 for comparison to a detection threshold or range, such as power, peak amplitudes, peak-to-peak differences, slopes, integrals, signal widths, spectral content, etc. The extracted feature or features are then analyzed at block 314 to determine goodness-of-fit (or lack-of-fit) metrics. Numerous detection algorithms may be developed for analyzing the compensated signal 312 using the extracted feature or features 900 for detecting a patient's physiological condition. Such algorithms may determine a match of the compensated signal with a normal patient condition or with a disease state. Detection algorithms may utilize morphological comparisons between the extracted feature or features 900 and known signal characteristics for a known patient condition, statistical methods, neural networks, or other models for determining a patient condition represented by the compensated signal. Generally, a detection algorithm may derive metrics from the extracted feature or features 900 that are compared to a detection threshold or range.

Figure 11:
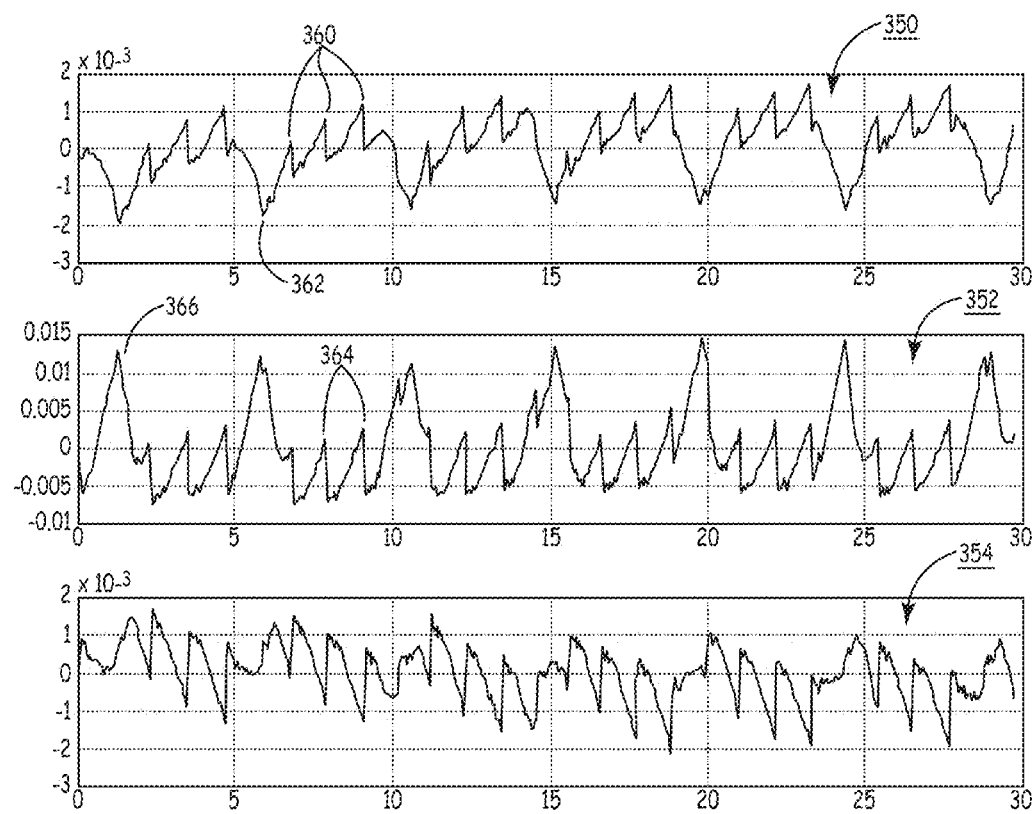
FIG. 11 shows recordings of a two-dimensional reflectance signal and a compensated signal computed for canceling ventilator artifact.

FIG. 11 shows recordings of a two-dimensional reflectance signal and a compensated signal computed for canceling ventilator artifact. In this example, R reflectance 350 is shown in the top panel, IR reflectance 352 is shown in the middle panel, and a compensated signal 354 is shown in the bottom panel. In the R reflectance 350, positive-going peaks 360 correspond to the signal response to cardiac pulsatility. Negative going peaks 362 correspond to the signal response to a ventilator. In the IR signal 352, small positive-going peaks 364 correspond to the signal response to cardiac pulsatility and large positive going peaks 366 correspond to the ventilator.

The compensated signal 354 is the result of computing the dot product of the incoming two-dimensional signal (R signal 350 and IR signal 352) and a principal component (e.g., the second principal component) orthogonal to the first principal component of the signal data during ventilation of the patient on a ventilator. The compensated signal 354 is a one-dimensional representation of the n-dimensional signal response to the cardiac variable with the ventilator artifact cancelled. Compensated signal 354 retains the significant variation due to cardiac pulsatility with variation of ventilator artifact removed. Features can be derived from compensated signal 354, for detecting a patient's heart rhythm.

The compensated signal provides a signal with reduced dimensions and artifact removed, thereby promoting more reliable and efficient detection of patient conditions than would occur using detection algorithms that analyze the uncompensated, n-dimensional signal. Various detection algorithms can be implemented using the compensated signal for detecting a patient condition. Such algorithms may compute features from the compensated signal, such as peak amplitudes, peak-to-peak differences, slopes, integrals, signal widths, spectral content, etc. Time dependent changes in the above features can also be derived as features. The feature or features are typically compared to a detection threshold or range. Detection algorithms may include morphology analysis, neural network algorithms or other detection algorithms designed to detect the patient condition from features extracted from the compensated signal.

Figure 12:
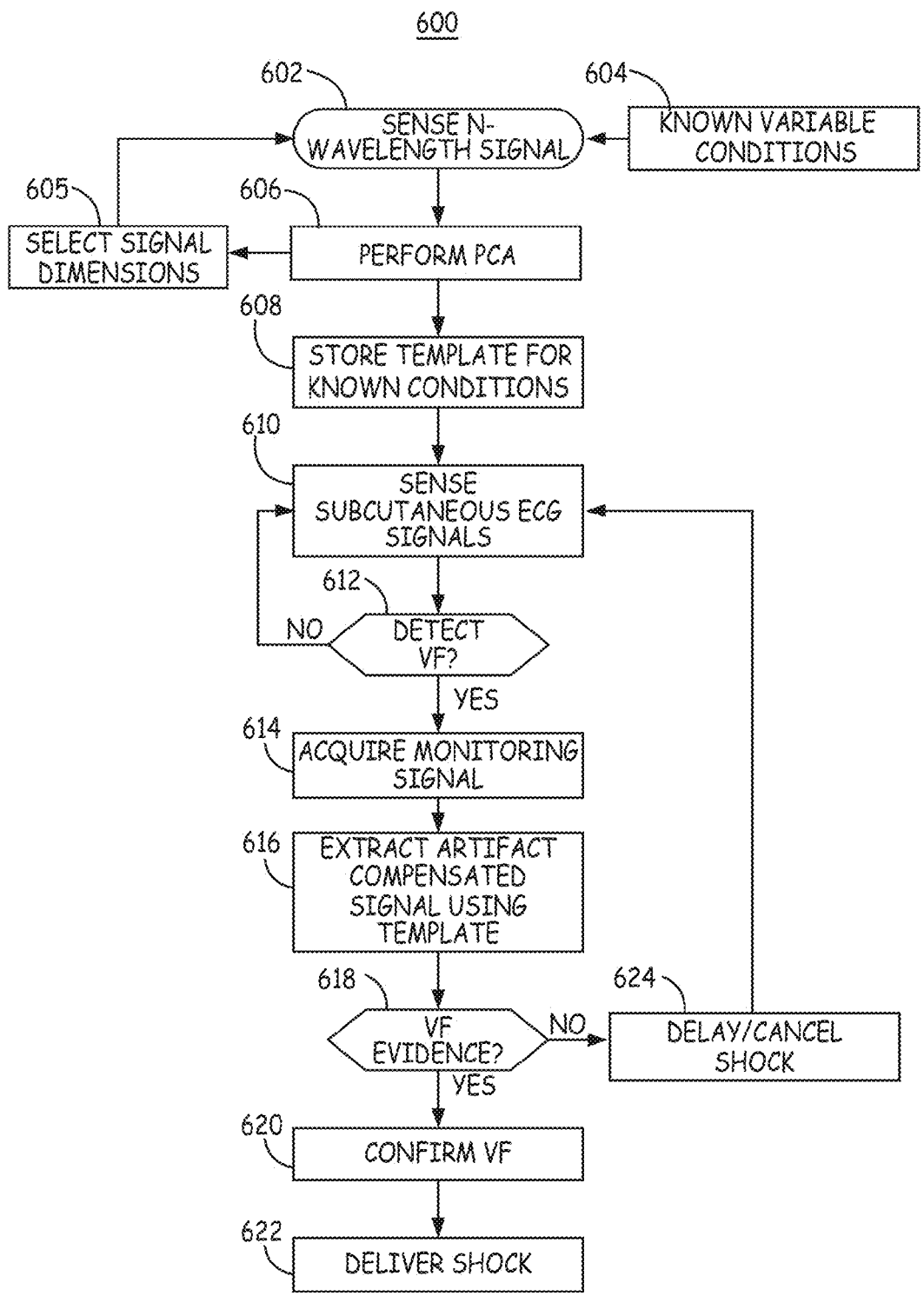
FIG. 12 is a flow chart of one method for signal processing and analysis using PCA for detecting a patient condition.

FIG. 12 is a flow chart of one method 600 for signal processing and analysis using PCA for detecting a patient condition. At block 602, a multi-wavelength reflectance signal is sensed during known variable conditions 604. PCA is performed at block 606 as described herein to compute a template for the known conditions. It is recognized for a given set of variable conditions, a template may include storing more than one principal component. The stored template may include the first principal component and/or one or more other principal components orthogonal to the first principal component.

Signal dimensions to be sensed or used during signal processing may be selected at block 605 based on the results of the PCA at block 606. The medical device controller may disable a sensor or cause the signal processing circuitry to ignore a signal dimension if that signal dimension is not contributing to the variation of the n-dimensional signal along a principal component. The value computed for that dimension in the principal component vector will be zero. In other words, the principal component will be defined by an eigenvector having a zero in at least one dimension, e.g., [x, y, 0]. The sensor or signal corresponding to a signal dimension having a zero contribution to a principal component can be disabled at block 205 or ignored during signal processing. Blocks 602 through 608 may be repeated for multiple sets of variable conditions, which may include known conditions for a variable of interest and/or known conditions for one or more artifacts.

At block 610, a subcutaneous ECG signal is sensed for detecting a heart rhythm. R-R intervals measured from the sensed ECG signal are analyzed and compared to arrhythmia detection criteria. If an arrhythmia is detected, for example if VF is detected as determined at decision block 612, the IMD controller enables monitoring of the n-wavelength reflectance signal at block 614. The monitoring signal and one or more stored templates are used to compute an artifact compensated signal at block 616. The artifact compensated signal is generally computed by determining a dot product of the n-dimensional monitored signal and an artifact template producing a 1-dimensional signal with artifact variation removed. It is recognized that in varying embodiments, a compensated signal may be computed using the monitored signal and one or more templates corresponding to the cardiac variable and/or artifacts.

The extracted compensated signal with reduced artifact content is analyzed for evidence of VF at block 618. The analysis performed at block 618 will depend on the compensated signal characteristics and may include threshold comparisons or other analysis of the compensated signal features.

If VF evidence is detected, the VF is confirmed at block 620 and the IMD controller can make an appropriate decision to deliver a defibrillation shock at block 622. If VF evidence is not detected in the compensated signal for confirming the ECG-based VF detection, the IMD controller may delay or cancel a defibrillation shock at block 624 to allow method 600 to return to block 610 to perform further sensing and analysis of the ECG signals and optionally other sensor signals. In this way, unnecessary defibrillation shocks to the patient can be avoided.

Figure 13:
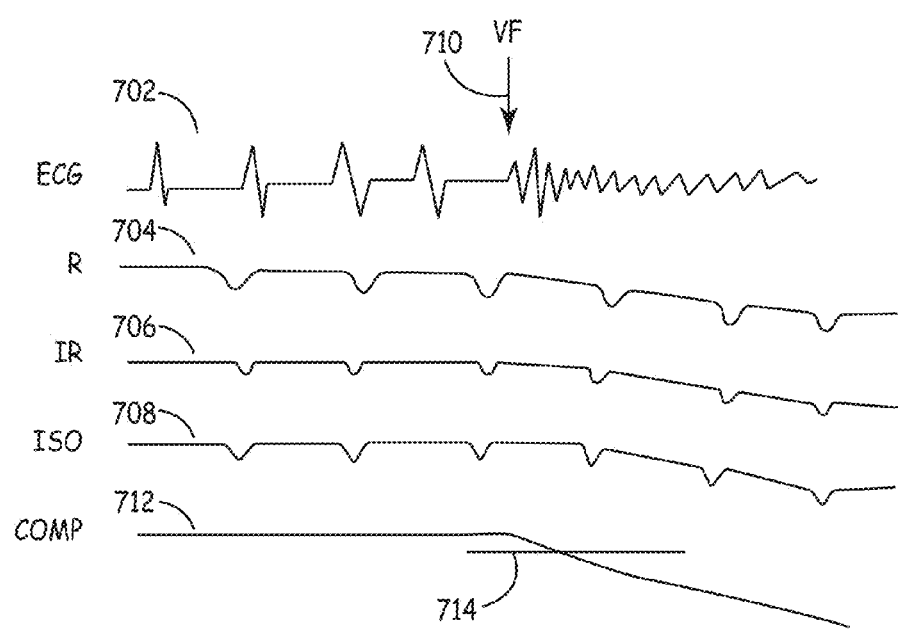
FIG. 13 is an example of three-dimensional reflectance signal during normal sinus rhythm and VF.

FIG. 13 is an example of three-dimensional reflectance signal during normal sinus rhythm and VF. ECG signal 702 represents normal sinus rhythm up until the onset of VF at 710. A R reflectance 704, an IR reflectance 706 and an Isobestic (ISO) reflectance 708 are each observed to include peaks associated with ventilator artifact. Each of these reflectances 704, 706 and 708 begin to decrease upon the onset of VF. However, the ventilator artifact may interfere with prompt detection of the decrease associated with VF. A compensated signal 712 is the scalar output of the dot product of the three-dimensional reflectance signal and a ventilator artifact principal component template acquired during a training period. The ventilator artifact is removed from the compensated signal 712 providing a "clean" 1-D reflectance signal that can be used for detecting VF. For example, when the compensated signal 712 falls below a threshold 714, VF detection is confirmed.

Thus, signal processing methods and apparatus have been presented in the foregoing description with reference to specific embodiments. It is appreciated that various modifications to the referenced embodiments may be made without departing from the scope of the invention as set forth in the following claims.

The invention claimed is:

1. A medical device, comprising:
a sensor for sensing an n-dimensional signal during a first time interval of a first known variable condition that influences the n-dimensional signal and during a second time interval of a second known variable condition that influences the n-dimensional signal different from the first known variable condition;
a processor configured to perform principal component analysis (PCA) on the sensed n-dimensional signal to generate a first template of a principal component of variation for the first known variable condition and a second template of a principal component of variation for the second known variable condition;
a storage device storing the first template and the second template; and
a controller configured to receive the n-dimensional signal during an unknown condition and detect a patient condition using the n-dimensional signal that is sensed during the unknown condition and at least one of the stored templates.

2. The device of claim 1, wherein the processor generates one or more principal components orthogonal to the principal component corresponding to the first known variable condition, and determines a reduced multi-dimensional signal sensed during the first known variable condition having less than n-dimensions.

3. The device of claim 2, wherein the processor generates one or more principal components orthogonal to the principal component corresponding to the second known variable condition, and determines a reduced multi-dimensional signal sensed during the second known variable condition having less than n-dimensions.

4. The device of claim 1, wherein the first known variable condition corresponds to pathological condition and the second known variable condition corresponds to a non-pathological condition.

5. The device of claim 1, wherein both the first known variable condition and the second known variable condition correspond to a non-pathological condition.

6. The device of claim 1, wherein the n-dimensional signal corresponds to a signal having one of different signal dimensions, different signal frequencies, different sensor positions within a body, different operating frequencies of the sensor or sensors, or other signal aspects separable according to time, frequency, space or sensor type.

7. The device of claim 1, wherein the processor computes a convergence metric to determine when signal data has converged within an acceptable range of variation for generating the first principal component and the second principal component and terminates the PCA on the sensed n-dimensional signal and stores the templates in response to the computed convergence metric.

8. The device of claim 1, wherein the first known variable condition and the second known variable condition correspond to one of multiple states for a given variable and different combinations of variables.

9. The device of claim 1, wherein, the processor selects, in response to the performed PCA, signal dimensions of the n-dimensional signal to be utilized by the controller during the detecting.

10. The device of claim 9, wherein the processor disables a signal dimension of the n-dimensional signal in response to the signal dimension not contributing to variation of the n-dimensional signal of the principal component.

11. The device of claim 1, further comprising an electrode sensing a cardiac signal that is received by the controller, wherein, in response to detecting a predetermined arrhythmia in response to the received sensed cardiac signal, the controller monitors subsequent n-dimensional signals sensed by the sensor to generate an n-dimensional monitoring signal, determines a compensated signal having fewer than n-dimensions using PCA in response to the monitoring signal and one or both of the templates, and confirms detecting of the predetermined arrhythmia in response to the compensated signal.

12. A method of generating a template in a medical device, comprising:
sensing an n-dimensional signal during a first time interval of a first known variable condition that influences the n-dimensional signal;
sensing the n-dimensional signal during a second time interval of a second known variable condition that influences the n-dimensional signal different from the first known variable condition;
performing principal component analysis (PCA) on the sensed n-dimensional signal sensed for the first known variable condition to generate a first template of a principal component of variation for the first known variable condition;
performing principal component analysis (PCA) on the sensed n-dimensional signal sensed for the second known variable condition to generate a second template of a principal component of variation for the second known variable condition;
storing the first template and the second template;
sensing the n-dimensional signal during an unknown condition; and
detecting a patient condition using the n-dimensional signal sensed during the unknown condition and at least one of the stored templates.

13. The method of claim 12, wherein performing principal component analysis (PCA) on the sensed n-dimensional signal sensed for the first known variable condition further comprises:
generating one or more principal components orthogonal to the principal component corresponding to the first known variable condition; and
reducing the n-dimensional signal sensed during the first known variable condition to an m-dimensional signal in response to the generated one or more orthogonal principal components, wherein m is less than n.

14. The method of claim 13, wherein performing principal component analysis (PCA) on the sensed n-dimensional signal sensed for the second known variable condition further comprises:
generating one or more principal components orthogonal to the principal component corresponding to the second known variable condition; and
reducing the n-dimensional signal sensed during the second known variable signal to an m-dimensional signal in response to the one or more orthogonal principal components, wherein m is less than n.

15. The method of claim 12, wherein the first known variable condition corresponds to pathological condition and the second known variable condition corresponds to a non-pathological condition.

16. The method of claim 12, wherein both the first known variable condition and the second known variable condition correspond to a non-pathological condition.

17. The method of claim 12, wherein the n-dimensional signal corresponds to a signal having one of different signal dimensions, different signal frequencies, different sensor positions within a body, different operating frequencies of the sensor or sensors, or other signal aspects separable according to time, frequency, space or sensor type.

18. The method of claim 12, further comprising computing a convergence metric to determine when signal data has converged within an acceptable range of variation for generating the first principal component and the second principal component.

19. The method of claim 12, wherein the first known variable condition and the second known variable condition correspond to one of multiple states for a given variable and different combinations of variables.

20. The method of claim 12, further comprising selecting, in response to the performed PCA, signal dimensions of the n-dimensional signal to be utilized during the detecting.

21. The method of claim 20, further comprising disabling a signal dimension of the n-dimensional signal in response to the signal dimension not contributing to variation of the n-dimensional signal of the principal component.

22. The method of claim 12, further comprising:
sensing a cardiac signal via a sensing electrode;
detecting a predetermined arrhythmia in response to the sensed cardiac signal;
monitoring subsequently sensed n-dimensional signals, in response to detecting the arrhythmia, to generate an n-dimensional monitoring signal;
determining a compensated signal having fewer than n-dimensions using PCA in response to the monitoring signal and one or both of the templates; and
confirming the detection of the predetermined arrhythmia in response to the compensated signal.

23. The device of claim 1, further comprising enabling the processor to generate the first template from the n-dimensional signal during a first time interval when a first condition of a variable of interest is known and to generate the second template during a second time interval when a second condition of the variable of interest is known, the second condition of the variable of interest different than the first condition.

24. The method of claim 12, further comprising:
generating the first template from the n-dimensional signal sensed during a first time interval when a first condition of a variable of interest is known; and
generating the second template from the n-dimensional signal sensed during a second time interval when a second condition of the variable of interest is known, the second condition of the variable of interest different than the first condition of the variable of interest.

* * * * *